(12) United States Patent
Misselbrook

(10) Patent No.: US 6,872,689 B1
(45) Date of Patent: Mar. 29, 2005

(54) WATER-DISPERSIBLE AGROCHEMICAL COMPOSITIONS

(75) Inventor: John Misselbrook, Southampton (GB)

(73) Assignee: Agform, Ltd. (GB)

( * ) Notice: Subject to any disclaimer, the term of this patent is extended or adjusted under 35 U.S.C. 154(b) by 0 days.

(21) Appl. No.: 10/069,911

(22) PCT Filed: Aug. 25, 2000

(86) PCT No.: PCT/GB00/03307

§ 371 (c)(1),
(2), (4) Date: Jul. 8, 2002

(87) PCT Pub. No.: WO01/13721

PCT Pub. Date: Mar. 1, 2001

(30) Foreign Application Priority Data

Aug. 26, 1999 (GB) .............................................. 9920281

(51) Int. Cl.[7] .............................................. A01N 25/14

(52) U.S. Cl. ....................... 504/128; 504/129; 504/133; 504/136; 504/367; 514/952

(58) Field of Search ................................ 504/128, 129, 504/133, 136, 367; 514/952

(56) References Cited

U.S. PATENT DOCUMENTS

| | | | |
|---|---|---|---|
| 4,065,289 A | | 12/1977 | Judd .............................. 71/82 |
| 5,372,989 A | * | 12/1994 | Geigle et al. ................ 504/116 |
| 5,474,971 A | | 12/1995 | Sandell ........................ 504/212 |
| 6,492,301 B1 | * | 12/2002 | Hacker et al. ............... 504/128 |

* cited by examiner

*Primary Examiner*—S. Mark Clardy
(74) *Attorney, Agent, or Firm*—Patents & TMS, P.C.

(57) ABSTRACT

The invention relates to novel compositions of biologically active agents containing less than 50% by weight of a low use rate agrochemical active and a dispersing agent, which exhibit enhanced bio-availability on dilution and application in water.

31 Claims, No Drawings

WATER-DISPERSIBLE AGROCHEMICAL COMPOSITIONS

The invention relates to novel chemical compositions in particular, compositions of biologically active agents and their use. The invention is more particularly concerned with granular compositions of low dose-rate agrochemicals, for example pesticides, suitably prepared by an extrusion process, which deliver the active ingredient of the composition efficiently to the substrate, for example a crop, which is to be treated.

The advantages of dispersible granule formulations of pesticides are known and include their ease of handling and reduced worker exposure compared to powder or liquid formulations. G. A. Bell, "Chemistry and Technology of Agrochemical Formulations", Edited by D. A. Knowles (Kluver, 1998), pages 80–114, describes a range of dispersible granule types and processes for their manufacture Dispersible granules may be prepared by extrusion. U.S. Pat. No. 3,954,439 discloses granular compositions of a herbicidal agent and one or more surfactants and processes for the production of such compositions. The process described in U.S. Pat. No. 3,954,439 is applicable to those herbicides which are substantially insoluble in water. This patent states that it is obviously desirable that the granules should have the highest possible content of active herbicidal material. This patent further states that the process is preferably carried out so as to give granules containing at least 50% of active herbicide material and that it is more preferable that the granules should contain more than this, that is at least 80% and even up to 95%. The patent also teaches that it is obviously important to keep the surfactant content down to a minimum, the total amount of surfactant preferably being from 5 to 15%

U.S. Pat No. 5,872,078 relates to dry, water soluble and/or water dispersible, agriculturally acceptable herbicidal compositions containing N-phosphonomethylglycerine or acceptable water-soluble salt thereof The composition may comprise further optional ingredients, one of which may be a co-herbicide A large number of co-herbicides are listed including sulfonylureas such as those available under the trade names Ally, Classic, Oust, Glean and mixtures thereof. A liquid surfactant is added to this mixture and extrusion granulation may be used to process the compositions described to form granules.

Improved delivery and bioavailability of the active ingredient in agrochemical compositions, especially of water insoluble actives for example sulphonyl ureas, to achieve a desired agrochemical effect is desirable. It is also desirable to achieve this effect in as cost effective manner as possible and conventionally this has been achieved by including as high a level of active ingredient as possible in a formulated composition.

We have now surprisingly found that a composition containing a lower level of a primary active ingredient than conventionally employed in compositions containing the same ingredient, together with a suitable dispersing agent may conferenhanced delivery of the primary active ingredient to the crop to be treated. The invention is particularly applicable to a low use rate agrochemical for instance a pesticide, and especially a water-insoluble agrochemical. Furthermore, as this enhanced effect may be achieved at a lower level of active ingredient in the composition, the composition may include additional materials in the remaining "formulation space" to provide additional effects Accordingly, a first aspect of the invention provides an agrochemical composition comprising a primary agrochemical active ingredient, preferably a low use rate active ingredient, at a level of less than 50% by weight of the composition and a dispersing agent, preferably a nonionic and/or anionic surfactant(s)

The compositions according to the first aspect of the invention provide surprisingly beneficial bioavailability of the active for instance by making a larger proportion of the active biologically available in a liquid carrier, for example water, with which the composition is mixed in use than a known composition having a high level of active. The compositions disperse rapidly in the liquid carrier to form stable suspensions of the active material(s) and subsequently dissolve at a rate and to an extent higher than that achieved by conventional compositions containing the same ingredients This property provides enhanced efficacy of the agrochemicals with attendant reduced crop damage This enhanced bioavailability means that a given agrochemical effect may be obtained using a lower total amount of agrochemical active thus providing environmental benefits through lower use of agrochemicals Further, as the concentration of the active is lower than conventionally employed, there is a reduced risk that some of the active will not be dispersed or dissolve in the liquid carrier. Hence the risk of poor disperion or dissolution of the active in a liquid carrier leading to high localised concentrations of the active penetrating to the crop especially the roots of plants and possibly damaging the crop is reduced A further advantage is that the lower level of primary active ingredient provides enhanced flexibility in formulating a composition as compared to conventional compositions employing high levels of active. Thus, the formulator may include a secondary active ingredient or other materials as desired in the composition to provide an optimum effect or balance of properties.

It has also been surprisingly found that when low use-rate pesticides, such as water-insoluble compounds including sulfonyl ureas, for example as described in U.S. Pat. No. 5,872,078, are employed as the primary active ingredient with a secondary high rate use pesticide and a suitable dispersing agent at the required level, the rate and extent of solubility and thus the bioavailability, of the primary active or both the actives may be increased as compared to granules containing the equivalent amount of each material alone. Optimally, the primary and secondary actives are intimately mixed in suitable proportions. Suitably, optional conventional other ingredients such as one or more additional surfactants are included in the formulation and the ingredients are processed into a suitable form, for example water-dispersible granules.

Accordingly the invention also provides in a preferred embodiment an agrochemical composition comprising as a primary active ingredient, a low use rate agrochemical active ingredient, at a level of less than 50% by weight of the composition and a secondary active ingredient, preferably a high use rate active ingredient, and a dispersing agent, preferably an anionic and/or nonionic surfactant.

In addition to the advantages referred to above for composition according to the invention, the compositions provide at least an enhanced effect as regards the primary active and suitably an effect greater than the combined additive affect of both the primary and secondary active is observed where the composition contains a primary and secondary active.

The term "low use rate" active denotes those agrochemical actives which typically are applied at a rate of less than 100 g/hectare and the term "high use rate" active denotes those agrochemical actives which typically are applied at a rate of more than 1000 g/hectare.

The compositions of the present invention result in the individual components being used at lower rates and with less phytotoxicity than conventional compositions of the said active materials, against a wide range of pests and diseases.

The level of primary active ingredient is suitably selected according to the particular compound to be used but is preferably less than 30% by weight of the composition, especially in the case of a low use rate active. For example, chlorsulfuron may suitably be employed at a level of less than 30%, for example 25% by weight of the composition. In a preferred embodiment, the primary active ingredient, for example bensulfuron, is present at a level of less than 10% and more preferably less than 2% by weight of the composition. In an especially preferred embodiment the primary active is present at a level of less than 1%. Suitably, the composition will contain the primary active at a level at which, on mixing with a liquid carrier, it provides a concentration of active which will provide a benefical effect in treating crops. This level may suitably be at 0.05% but is preferably at least 0.1% and desirably at least 0.2% by weight of the composition although the precise level may be adjusted according to the particular application and the particular primary active present in the composition.

Where a second active is employed, it is suitably present at a level greater than the level of the primary active ingredient. In a preferred embodiment the secondary active is present at a level of at least 30%, more preferably at least 50%, optimally at least 65%, for example 75% by weight of the composition The invention comprises a dry, free-flowing, dustless and rapidly dispersing granular formulation containing a low use rate pesticide or mixture of pesticides together with an additional high use rate pesticide. The terms composition and formulation are used herein to have the same meaning.

A suitable dispersing agent(s) is/are incorporated into the formulation at a specific ratio so as to enable the rapid dispersion and subsequent dissolution of the low use rate and high use rate active material upon dilution and subsequent application. Suitably, the weight ratio of dispersing agent to the low use rate primary active ingredient in the composition is 0.1 to 10:1, preferably 0.4 to 6:1, for example about 4:1 and about 5:1.

The invention is particularly suitable for, but not limited to, such low use-rate pesticides as: Abamectin, imidazolinone, azoxystrobin, bensulfuron-methyl carfentrazone-ethyl, chlorsulfuron, cinosulfuron, clodinafop, clopyralid, lambda-cyhalothrin, deltamethrin, diflufenican, emamectin benzoate, fibronil, flurtamone, imazamethabenz-methyl, imazapyr, imazethapyr, imadacloprid, metsulfuron-methyl, milbectin, nicosulfuron, pirimisulfuron-methyl, rimsulfuron, sulfometuron-methyl, thifensulfuron-methyl, tribenuron-methyl, and tirflusulfuron-methyl. Preferably the low use rate pesticide is a sulfonyl urea.

Suitable high use rate pesticides include: Abamectin, atrazine, benomylbentazone, bifenox, bromoxynil, captan, carbendazim, chloridazon, chlorothalonil, chlortoluron, lambda-cyhalothrin, cyhexatin, cymoxynil, alpha-cypermethrin, deltamethrin, dimethomorph, diuron, ethofumesate, fibronil, flurtamone, glyphosate, imazamethabenz-methyl, imazapyr, imazethapyr, imadacloprid, isoproturon, linuron, mancozeb, maneb, metamitron, methiocarb, metribuzin, milbectin, oxadixyl, oxyfluorfen, phenmedipham, propanil, propyzamide, simazine, thifensulfuron-methyl and thiram.

In an especially preferred embodiment, the low use rate pesticide comprises bensulfuron-methyl and the high use rate pesticide comprises propanil.

In a preferred embodiment, the dispersing agent comprises a surfactant with nonioic surfactants and especially anionic surfactants being preferred. Examples of suitable dispersing agents include alkali metal, preferably sodium salts of lignosulphonates, naphthalene sulphonate formaldehyde condensates, tristyrylphenol ethoxylate phosphate esters, aliphatic alcohol ethoxylates, alkylphenol ethoxylates, ethylene oxide/propylene oxide (EO-PO) block copolymers, "comb" graft copolymers and polyvinyl alcohol-vinyl acetate copolymers. Other dispersing agents known in the art may be employed as desired.

In addition to the dispersing agent, other components may be present in the composition for example a wetting agent. Suitable wetting agents include: alkali metal salts of alkylaryl sulphonates, alkyl aryl sulphosuccinates and alkyl sulphates, preferably as the sodium salt. Other wetting agents, and other excipients known to those skilled in the art may be employed as desired including disintegrants for example: Bentonite, modified starch and polyvinyl pyrrolidone; stabilisers, for example citric acid, polyethylene glycol and butylated hydroxy toluene; and fillers, for example, starch, lactose, china clay, sucrose and kaolin; and flow-aids.

The granular compositions are preferably prepared by the method described in PCT application PCT/GB00/00163 the contents of which are hereby incorporated by reference. Suitably the process comprises, preparing a mix in the form of a free-flowing powder, preferably a homogeneous powder, comprising the primary active ingredient and a dispersing agent and optionally other components, preferably without forming a paste, and extruding the pre-mix in an extruder, for example a low pressure extruder to form the granules. A pre-mix optionally containing the secondary active ingredient may be mixed with the dispersing agent and the primary active ingredient to form the mix for extrusion. The dispersing agent may be liquid in which case an additional liquid component is not required although a further liquid component may be included as desired.

Suitable apparatus for the blending step(s) include a low-shear, high intensity blender such as a Lodige Ploughshare mixer, ribbon, Y-cone, double cone or trough blender, so that a free-flowing powder is formed. The mix is fed directly or indirectly into a suitable low-pressure extruder, such as that described in WO 96/26828, so that the premix is compacted against the apertures in the screen and forced through.

In a preferred embodiment, the composition of the mix and the extruder settings are such that the formation of a paste before extrusion is avoided and the material being processed remains a free flowing particulate material during the formation of the pre-mix. In particular, the material optimally does not form a paste prior to extrusion. However, as the composition may contain one or more liquid components, it may be wet or dry provided that it remains free-flowing and particulate during the process. In this context, a paste may be considered as a mass of material for example an agglomerate, which contains sufficient liquid or is at such a temperature that the particulate material being processed forms into an agglomerate which is mouldable or deformable and which is not free-flowing Thus, a paste does not disintegrate into finer particles on application of shear, for example by rubbing between fingers, but rather remains as an agglomerated mass and the shear acts to mould or deform the agglomerate.

If desired, the components of the composition, either in sequence, all together or some in sequence and others together are first mixed, for example in a blender so that a uniform blend is obtained which is then passed through a suitable milling system such as an air mill, pin mill or air-swept impact mill so that a fine powder (the pre-mix) comprising an average particle size of 0.5 to 20 microns, or more preferably between 0.5 to 5 microns is obtained. The powder thus obtained is suitably agglomerated, so that uniform, dust-free granules are obtained, preferably by the process described in PCT/GB00/00163. This preferred method involves the extrusion of the wetted powder which is then in the form of a freely flowing homogeneous powder, in a low temperature, low pressure extruder, for example as described in EP-A-812256.

Where present, the low use rate and high use rate agrochemicals may be combined in the formation of the dry pre-mix with the other formulation ingredients for example dispersing agents or alternatively the pre-mix may be prepared with one of the agrochemicals and the other added to the milled pre-mix. This alternative approach is preferred when the high use rate pesticide is propanil which is suitably incorporated in the dry pre-mix, and the low use rate pesticide is then added to the pre-mix and blended with it prior to granulation.

In a second aspect, the invention provides a method of treating a plant by applying a herbicidally effective amount of a composition according to the present invention to the plant or to the locus of the plant.

The present invention enables the composition of the invention to be used at a lower rate of use (mass of composition/unit area, typically grammes per hectare) to achieve a given effect than known compositions. Suitably the agrochemical active is applied to the plant or locus of the plant at a rate of use of less than 75%, more preferably less than 50% of the conventional rate of use for the active in commercially available compositions.

In a preferred embodiment, a composition comprising a sulphonyl urea low use rate active for example bensulfuron, is applied in use at a rate of use of less than 50 g/hectare, especially less than 30 g/hectare and optimally less than 20 g/hectare. Typically, a commercially available composition containing in excess of 50% by weight of the composition of bensulfuron-methyl may be employed at a rate of use of 60 g/hectare or more. In another preferred embodiment, the composition comprises a high use rate secondary active comprising propanil in addition to a sulphonyl urea active, for example bensulfuron, and suitably the secondary active is applied in use at a rate of less than 7000 g/hectare, preferably less than 5000 g/hectare and especially at a rate of less than 3200 g/hectare Where the plant is a weed, suitably, the treatment is such as to control or kill the weed. Generally, the composition is applied to the plant or its locus by means of a liquid carrier, typically water, with which the composition is mixed prior to application. If desired, the composition may be mixed with a liquid carrier to form a concentrate suitable for subsequent mixing with a liquid carrier The application of the composition to the plant or its locus in solid or concentrate form especially where water is present in the vicinity of the plant through natural precipitation is also within the ambit of the invention.

In water, suitably the composition is diluted for use to a level of 10 to 500 mg/l and preferably 20 to 300 mg/l The dilution is suitably selected according to the composition used, the type of application, the state of growth of the plants to be treated and other factors known to those skilled in the art.

In a third aspect, the invention provides for use of a composition according to the invention as an agrochemical, for example a low use rate herbicide.

This invention relates to novel compositions and to methods of treating plants, for example killing or controlling weeds by applying a reduced amount of the active ingredient (s), suitably diluted in water, than that normally recommended for such active(s) against such weeds. In addition the invention allows for the avoidance of subsequent applications of the said actives, thus further reducing the amount of pesticide used.

The following examples illustrate the invention in an non-limiting manner.

EXAMPLE 1

Chlorsulfuron 25 WG

| Ingredient | Trade name | % w/w |
|---|---|---|
| Chlorosulfuron technical (95%) | (technical a.i.) | 26.32 |
| Sodium lignosulfonate | Ultrazine NA | 12.50 |
| Dodedyl benzene sulphonate, Sodium salt | Arylan SX85 | 5.00 |
| Lactose | Lactose | 56.18 |

Method

The chlorsulfuron technical was airmilled using a Gem-T airmill before combining with other components The technical, Ultrazine and Arylan components were blended until uniform ni a high speed blender. The lactose was then added and the formulation blended for a further 15 seconds. 12% distilled water was added whilst blending. The wetted premix (free flowing powder) was fed to a basket extruder as described in EP-A-812256 through a 1 mm screen. A compacted extrudate was obtained and the resulting granules dried at 60 C for 8 minutes The dried granules were then sieved through 2 mm and 500 micron sieves.

Comparative Example A

Chlorsulfuron 75 WG

| Ingredient | Trade name | % w/w |
|---|---|---|
| Chlorsulfuron technical (95%) technical a.i.) | | 75.95 |
| Sodium lignosulfonate | Ultrazine NA | 12.50 |
| Di isopropyl naphthalene sulfonate, sodium salt | Galoryl MT704 | 1.00 |
| Lactose | Lactose | 7.55 |

Method

The chlorsulfuron technical was airmilled using a Gem-T airmill before combining with other components The milled chlorsulfuron technical, Ultrazine and Galoryl components were blended until uniform in a high speed blender. The lactose was then added and the formulation blended for a further 15 seconds. 17% distilled water was added whilst blending. The wetted premix (free flowing powder) was fed to a basket extruder as described in EP-A-812256 through a 1 mm screen A compacted extrudate was obtained and the resulting granules dried at 60 C for 8 minutes. The dried granules were then sieved through 2 mm and 500 micron sieves.

The solubility of the compositions produced according to Example 1 and Comparative Example A and Glean (commercially available 75 WG product) and airmilled technical was tested using the method below:

Solubility Test Method 200 mls water was poured into a jacketed glass vessel and allowed to reach 25 C. A Grant recirculator was used to maintain the temperature at 25 C+/−1 C. A magnetic stirrer at a set speed was used to stir the water. The specified weight of granules was then added to the water and allowed to disperse for 30 seconds before a timer was started. A 2 mls sample was removed using a syringe after 5 minutes and filtered using a 0.45 micron syringe filter. The solution was then analysed to determine the active concentration using a HPLC method. The theoretical concentration assuming 100% solubility was calculated using an assay obtained using the HPLC.

The following data was obtained:

| Formulation | Product | Dilution rate (mgs a.i./L) | Type of water used to dilute granules | % active added to water that dissolved after 5 minutes |
|---|---|---|---|---|
| Example 1 | 25 WG | 69 | Distilled | 98 |
| Comparative Example A | 75 WG | 72 | Distilled | 95 |
| Glean (Du Pont) | 75 WG | 72 | Distilled | 67 |
| Airmilled technical | — | 91 | Distilled | <2 |

Conclusions

Both the 75 and 25 extruded WG formulations have a significantly higher solubility in distilled water compared to the commercial product. The technical is not readily soluble in distilled water at this temperature.

EXAMPLE 2

Bensulfuron-methyl 1 WG

| Ingredient | Trade name | % w/w |
|---|---|---|
| Bensulfuron methyl technical (95%) | (technical a.i.) | 1.05 |
| Naphthalene sulfonic acid Formaldehyde condensate, sodium salt | Galoryl DT505 | 12.70 |
| Di isopripyl naphthalene sulfonate, sodium salt | Galoryl MT704 | 1.00 |
| Lactose | Lactose | 85.25 |

Method

The technical and Galoryl DT505 were blended together until uniform. The blend was then airmilled using a Gem-T airmill. The milled premix, Galoryl MT704 and lactose were blended until uniform in a high speed blender The lactose was then added and the formulation blended for a further 15 seconds 12% distilled water was added whilst blending. The wetted premix (free flowing powder) was fed to a basket extruder as described in EP-A-812256 through a 1 mm screen A compacted extrudate was obtained and the resulting granules dried at 60 C for 8 minutes The dried granules were then sieved through 2 mm and 500 micron sieves Comparative Example B Bensulfuron-methyl 60 WG

| Ingredient | Trade name | % w/w |
|---|---|---|
| Bensulfuron methyl technical (95%) | (technical a.i.) | 64.21 |
| Naphthalene sulfonic acid Formaldehyde condensate, sodium salt | Galoryl DT505 | 12.70 |
| Di isopripyl naphthalene sulfonate, sodium salt | Galoryl MT704 | 1.00 |
| Lactose | Lactose | 22.08 |

The composition of Comparative Example B was prepared using the method set out in Example 2.

The solubility of the compositions of Example 2 and Comparative Example B were then tested using the method detailed in Example 1. The following data was obtained:

| Formulation | Product | Dilution rate (mgs a.i./L) | Type of water used to dilute granules | % active added to water that dissolved after 5 minutes |
|---|---|---|---|---|
| Londax | 60 WG | 300 | Tap | 12 |
| Comparative Example B | 60 WG | 291 | Tap | 25 |
| Londax | 60 WG | 75 | Tap | 19 |
| Comparative Example B | 60 WG | 73 | Tap | 46 |
| Example 2 | 1 WG | 240 | Tap | 71 |

EXAMPLE 3

Propanil and bensulfuron-methyl Combined WG (75% Propanil and 0.75% Bensulfuron)

Propanil Premix

A premix of Propanil was prepared as follows:

| Ingredient | Trade name | % w/w |
|---|---|---|
| Propanil technical (97 0% a.i) | Technical | 82.47 |
| Starch | Paselli | 1.00 |
| Nonionic surfactant and sodium Lignosulphonate blend | Stepsperse DF 500 | 5.00 |
| Modified sodium lignosulphonate | Ufoxane 3A | 5.00 |
| Hydrated aluminium silicate | China Clay | to1.00 |

The ingredients were blended in a medium shear, high speed blender for 5 minutes until uniform. The resulting mixture was passed through an air mill to obtain a fine powder. The powder was wetted with 19.5% water (based on the dry weight of powder) an blended until a damp free flowing powder was formed. The premix was used in the following blends with bensulfuron:

| Ingredient | Trade name | % w/w |
|---|---|---|
| Bensulfuron methyl technical (95%) | (technical a.i.) | 0.79 |
| Propanil 80% milled premix | — | 93.75 |
| Naphthalene sulfonic acid Fomaldehyde condensate, sodium salt | Galoryl DT505 | 0.31 |
| China clay | China clay GTY | 5.15 |

The technical and Galoryl DT505 were blended together until uniform. The blend was then airmilled using a Gem-T airmill. The milled bensulfuron-methyl and milled propanil premixes. Galoryl MT704 and china clay were blended until uniform in a high speed blender. 17% distilled water was added whilst blending. The wetted premix (free flowing powder) was fed to a basket extruder as described in EP-A-812256 through a 1 mm screen. A compacted extrudate was obtained and the resulting granules dried at 60 C for 8 minutes. The dried granules were then sieved through 2 mm and 500 micron sieves.

EXAMPLE 4

Propanil and bensulfuron-methyl Combined WG (75% Propanil and 0.375% Bensulfuron)

| Ingredient | Trade name | % w/w |
|---|---|---|
| Bensulfuron-methyl technical (95%) | (technical a.i.) | 0.39 |
| Propanil 80% milled premix | — | 93.75 |
| Naphthalene sulfonic acid Fomaldehyde condensate, sodium salt | Galoryl DT505 | 0.16 |
| China clay | China clay GTY | 5.70 |

The technical and Galoryl DT505 were blended together until uniform. The blend was then airmilled using a Gem-T airmill The milled bensulfuron-methyl and milled propanil premixes, Galoryl MT704 and china clay were blended until uniform in a high speed blender. 17% distilled water was added whilst blending The wetted premix (free flowing powder) was fed to a basket extruder as described in EP-A-812256 through a 1 mm screen. A compacted extrudate was obtained and the resulting granules dried at 60 C for 8 minutes. The dried granules were then sieved through 2 mm and 500 micron sieves The above combination formulations were tested using the solubility method detailed in Example 1 The following data was obtained:

| Formulation | % bensulfuron-methyl a.i. | Dilution rate (mgs a.i./L) | Type of water used to dilute granules | % active added to water that dissolved after 5 minutes |
|---|---|---|---|---|
| Example 3 | 0.75 | 75 | Tap | 66 |
|  | 0.75 | 112.5 | Tap | 64 |
| Example 4 | 0.375 | 37.5 | Tap | 83 |
|  | 0.375 | 56 | Tap | 84 |

Further solubility testing up to 2 hours was carried out using the same method as for Example 1 except the granules were diluted in 1000 mls water and samples were taken after 5, 30, 60 90 and 120 minutes The following results were obtained using 37.5 mgs a.i./liter (all in tap water). Data for Comparative Example B (bensulfuron-methyl 60 WG) and Londax (commercial bensulfuron-methyl 60 WG) at the same dilution rate is shown for comparison.

| | % active added to water that dissolved | | |
|---|---|---|---|
| Time (mins) | Example 5 | Comparative Example B | Londax |
| 5 | 67 | 42 | 15 |
| 30 | 67 | 52 | 32 |
| 60 | 67 | 57 | 39 |
| 90 | 66 | 57 | 49 |
| 120 | 69 | 62 | 53 |

Conclusions

The solubility rate of bensulfuron-methyl in a granule which also contains an active that is used a high rate per hectare, is significantly higher compared with diluting the bensulfuron-methyl as a 60 WG.

EXAMPLE 5

Propanil and bensulfuron-methyl Combined WG (75% Propanil and 0.24% Bensulfuron)

| Ingredient | Trade name | % w/w |
|---|---|---|
| Bensulfuron methyl technical (95%) | (technical a.i.) | 0.25 |
| Propanil 80% milled premix | — | 93.72 |
| Naphthalene sulfonic acid Fomaldehyde condensate, sodium salt | Galoryl DT505 | 0.10 |
| China clay | China clay GTY | 5.90 |

The processing method set out in Example 4 was employed, with the bensulfuron-methyl being milled as a premix with the Galoryl DT505. The solubility of the bensulfuron-methyl in the above formulation was then tested using the method set out in Example 4. The following results were obtained using 25 mgs and 31.3 mgs bensulfuron-methyl a.i./liter (in tap water).

| | % bensulfuron-methyl active added to water that dissolved | |
|---|---|---|
| Time (mins) | Example 5 (25 mgs/L) | Example 5 (31.3 mgs/L) |
| 5 | 89 | 91 |
| 30 | 90 | 92 |
| 60 | 94 | 92 |
| 90 | 93 | 96 |
| 120 | 97 | 95 |

Field Evaluation

A composition according to Example 4 was evaluated in the field in comparison with commercial formulations containing the same active ingredients.

Treatment Details

| Treatment Number | Composition | Rate of used (g/Hectare) Product |
|---|---|---|
| Control | Untreated Control | — |
| 1 | Stam 80 EDF | 4,000 g at Growth State BBCH 12–13 |
|  |  | 8,000 g at Growth Stage BBCH 21–21 |
| 2 | Stam 80 EDF + Londax 60 | 4,000 g at Growth Stage BBCH 12–13 100 g at Growth Stage BBCH 12–13 |
| 3 | Example 4 | 4,000 g at Growth Stage BBCH 12–13 |

The above treatments were applied in 400 l water/ha on Rice v.loto against Gramineae family weeds. The weeds were assessed at −1, +4, +16 and +32 days after application by the efficacy assessment guidelines provided by EPPO Guidelines PP1/181(2), PP1/152(2) and 1/62(2). Stam 80 EDF is a commercial formulation containing 80% propanil in the form of an extruded granule. Londax 60 is a commercial formulation containing 60% bensulfuron-methyl in the form of a fluid bed granule.

Results

Assessment: 1 day before 1st Application

|  | Control % cov. | Treatment 1 | | | Treatment 2 | | | Treatment 3 | | |
| --- | --- | --- | --- | --- | --- | --- | --- | --- | --- | --- |
|  |  | % cov | % eff. | Sympt. | % cov | % eff. | Sympt. | % cov | % eff. | Sympt. |
| Weeds |  |  |  |  |  |  |  |  |  |  |
| *Heteranthera lumasa* | 38.0 | 37.0 | 0.0 | n.a. | 35.0 | 0.0 | n.a. | 35.00 | 0.0 | n.a. |
| *Heteranthera reniformis* | 0.0 | 1.0 | 0.0 | n.a. | 0.0 | 0.0 | n.a. | 0.0 | 0.0 | n.a. |
| *Echinochloa crus-galli* | 1.0 | 1.0 | 0.0 | n.a. | 1.0 | 0.0 | n.a. | 1.0 | 0.0 | n.a. |
| *Panicum dichotamiflorum* | 1.0 | 1.0 | 0.0 | n.a. | 1.0 | 0.0 | n.a. | 1.0 | 0.0 | n.a. |
| *Scirpus maritimus* | 1.0 | 1.0 | 0.0 | n.a. | 1.0 | 0.0 | n.a. | 2.0 | 0.0 | n.a. |
| *Scirpus mucronatus* | 1.0 | 1.0 | 0.0 | n.a. | 2.0 | 0.0 | n.a. | 1.0 | 0.0 | n.a. |

Assessment: 4 days after 1st Application

|  | Control % cov. | Treatment 1 | | | Treatment 2 | | | Treatment 3 | | |
| --- | --- | --- | --- | --- | --- | --- | --- | --- | --- | --- |
|  |  | % cov | % eff. | Sympt. | % cov | % eff. | Sympt. | % cov | % eff. | Sympt. |
| Weeds |  |  |  |  |  |  |  |  |  |  |
| *Heteranthera lumasa* | 55.0 | 55.0 | 70.0 | WC | 34.0 | 80.0 | W | 40.0 | 50.0 | W |
| *Heteranthera reniformis* | 0.5 | 0.0 | 0.0 | n.a. | 0.6 | 0.0 | n.a. | 0.0 | 0.0 | n.a. |
| *Echinochloa crus-galli* | 7.0 | 0.0 | 0.0 | n.a. | 1.0 | 0.0 | n.a. | 1.0 | 0.0 | n.a. |
| *Panicum dichotamiflorum* | 5.5 | 0.0 | 0.0 | n.a. | 1.0 | 0.0 | n.a. | 1.0 | 0.0 | n.a. |
| *Scirpus maritimus* | 1.0 | 4.0 | 90.0 | W | 0.0 | 0.0 | n.a. | 3.0 | 70.0 | W |
| *Scirpus mucronatus* | 2.0 | 1.0 | 60.0 | W | 2.0 | 60.0 | W | 5.0 | 70.0 | W |

Assessment: 16 days after 1st Application

|  | Control % cov. | Treatment 1 | | | Treatment 2 | | | Treatment 3 | | |
| --- | --- | --- | --- | --- | --- | --- | --- | --- | --- | --- |
|  |  | % cov | % eff. | Sympt. | % cov | % eff. | Sympt. | % cov | % eff. | Sympt. |
| Weeds |  |  |  |  |  |  |  |  |  |  |
| *Heteranthera lumasa* | 55.0 | 1.0 | 99.0 | W.C. | 18.0 | 80.0 | W.C. | 2.0 | 98.0 | W |
| *Heteranthera reniformis* | 0.0 | 0.0 | 0.0 | n.a. | 0.0 | 0.0 | n.a. | 0.0 | 0.0 | n.a. |
| *Echinochloa crus-galli* | 10.0 | 0.0 | 0.0 | n.a. | 1.0 | 0.0 | n.a. | 0.0 | 0.0 | n.a. |
| *Panicum dichotamiflorum* | 15.0 | 0.0 | 0.0 | n.a. | 1.0 | 0.0 | n.a. | 0.0 | 0.0 | n.a. |
| *Scirpus maritimus* | 5.0 | 0.0 | 0.0 | n.a. | 0.0 | 0.0 | n.a. | 1.0 | 98.0 | W |
| *Scirpus mucronatus* | 15.0 | 0.0 | 0.0 | n.a. | 0.0 | 0.0 | n.a. | 0.0 | 0.0 | n.a. |

Assessment: 32 days after 1st Application

|  | Control % cov. | Treatment 1 | | | Treatment 2 | | | Treatment 3 | | |
| --- | --- | --- | --- | --- | --- | --- | --- | --- | --- | --- |
|  |  | % cov | % eff. | Sympt. | % cov | % eff. | Sympt. | % cov | % eff. | Sympt. |
| Weeds |  |  |  |  |  |  |  |  |  |  |
| *Heteranthera lumasa* | 37.0 | 0.0 | 0.0 | n.a. | 1.0 | 0.0 | n.a. | 0.0 | 0.0 | n.a. |

-continued

| Weeds | Control % cov. | Treatment 1 | | | Treatment 2 | | | Treatment 3 | | |
|---|---|---|---|---|---|---|---|---|---|---|
| | | % cov | % eff. | Sympt. | % cov | % eff. | Sympt. | % cov | % eff. | Sympt. |
| *Heteranthera reniformis* | 1.0 | 0.0 | 0.0 | n.a. | 0.0 | 0.0 | n.a. | 0.0 | 0.0 | n.a. |
| *Echinochloa crus-galli* | 10.0 | 0.0 | 0.0 | n.a. | 0.0 | 0.0 | n.a. | 0.0 | 0.0 | n.a. |
| *Panicum dichotamiflorum* | 15.0 | 0.0 | 0.0 | n.a. | 2.0 | 0.0 | n.a. | 0.0 | 0.0 | n.a. |
| *Scirpus maritimus* | 5.0 | 0.0 | 0.0 | n.a. | 0.0 | 0.0 | n.a. | 0.0 | 0.0 | n.a. |
| *Scirpus mucronatus* | 32.0 | 0.0 | 0.0 | n.a. | 0.0 | 0.0 | n.a. | 0.0 | 0.0 | n.a. |

Abbreviations
% cov. % area covered by weeds
% eff.: % herbicide efficacy (% of weeds showing necrotic symptoms):
Sympt. symptoms (W withered; C:chlorotic; n.a. not applicable)

Conclusions

The above results demonstrate the composition of Example 4 (15 g/ha bensulfuron-methyl combined with 3,000 g/ha propanil) provides equivalent control to the commercial products tested when applied at less than ⅓rd of the propanil in the Stam 80 EDF treatment (two applications, one 3200 a.i. g/ha and one 6400 a.i. g/ha propanil) and ¼ of the Londax rate (one application of 60 g/ha bensulfuron-methyl tank mixed with one application of 3,200 g/ha propanil).

What is claimed is:

1. A water dispersible agrochemical composition comprising a primary agrochemical active ingredient at a level of less than 50% by weight of the composition and a dispersing agent the composition being obtainable by a process comprising preparing a wetted mix in the form of a free-flowing powder comprising the primary active ingredient and the dispersing agent and optionally other components wherein at least one of the dispersing agent and optional other component is liquid and extruding the mix to form granules.

2. A composition according to claim 1 in which the primary active ingredient is a low use rate active ingredient.

3. A composition according to claim 2 further comprising as the low use rate active ingredient, bensulfuron-methyl and further comprising propanil.

4. A composition according to claim 3 in which bensulfuron-methyl is present at a level of less than 1% by weight of the composition and propanil is present at a level of more than 50% by weight of the composition.

5. A composition according to claim 1 in which the primary active ingredient comprises bensulfuron-methyl and/or chlorsulfuron.

6. A composition according to claim 5 comprising bensulfuron-methyl at a level of less than 10% by weight of the composition.

7. A composition according to claim 1 further comprising a high use rate secondary active ingredient.

8. A composition according to claim 7 in which the secondary active ingredient is present at a level greater than the level of the primary active ingredient.

9. A composition according to claim 7 in which the secondary active ingredient is present at a level of at least 30%.

10. A composition according to claim 7 in which the high use rate secondary active ingredient is selected from abamectin, atrazine, benomyl, bentazone, bifenox, bromoxynil, captan, carbendazim, chloridazon, chlorothalonil, chlortoluron, lambda-cyhalothrin, cyhexatin, cymoxynil, alpha-cypermethrin, deltamethrin, dimethomorph, diuron, ethofumesate, fipronil, flurtamone, glyphosate, imazamethabenz-methyl, imazapyr, imazethapyr, imidacloprid, isoproturon, linuron, mancozeb, maneb, metamitron, methiocarb, metribuzin, milbectin, oxadixyl, oxyfluorfen, phenmedipham, propanil, propyzamide, simazine, thifensulfuron-methyl and thiram.

11. A composition according to claim 10 in which the secondary active ingredient comprises propanil.

12. A composition according to claim 11 in which the propanil is present at a level of at least 50% by weight of the composition.

13. A composition according to claim 1 in which the dispersing agent comprises an anionic and/or nonionic surfactant.

14. A composition according to claim 13 in which the dispersing agent is selected from alkali metal salts of lignosulphonates, naphthalene sulphonate formaldehyde condensates, tristyrylphenol ethoxylate phosphate esters, aliphatic alcohol ethoxylates, alkylphenol ethoxylates, ethylene oxide/propylene oxide (EO-PO) block copolymers, "comb" graft copolymers and polyvinyl alcohol-vinyl acetate copolymers.

15. A composition according to claim 13 in which the weight ratio of dispersing agent to the low use rate primary active ingredient in the composition is 0.1 to 10:1.

16. A composition according to claim 13 in which the weight ratio of dispersing agent to the low use rate primary active ingredient in the composition is 0.4 to 6:1.

17. A composition according to claim 1 in which the primary active ingredient is selected from bensulfuron-methyl, chlorsulfuron, cinosulfuron, metsulfuron-methyl, nicosulfuron, pirimisulfuron-methyl, rimsulfuron, sulfometuron-methyl, thifensulfuron-methyl, and triflusulfuron-methyl.

18. A composition according to claim 1 in which the primary active ingredient is present at a level of less than 30% by weight of the composition.

19. A composition according to claim 1 wherein the primary agrochemical active comprises a sulfonyl urea.

20. A composition according to claim 1 wherein the liquid component in the wetted premix comprises water.

21. A composition according to claim 1 wherein the extrudate is dried to form granules.

22. A method of treating a plant by applying a herbicidally effective amount of a composition according to any one of claims 1 to 18 to the plant or to the locus of the plant to be treated.

23. A method according to claim 22 in which the composition is mixed with a liquid carrier and applied to the plant or the locus of the plant.

24. A method according to claim 22 in which the primary active is applied to the plant or the locus of the plant at a rate of use of less than 50 g/hectare.

25. A method according to claim 22 in which the composition comprises, as a secondary active ingredient, propanil and the secondary active is applied to the plant or the locus of the plant at a rate of use of less than 7000 g/hectare.

26. A process for the production of a composition according to claim 1 comprising preparing a wetted mix in the form of a free-flowing powder comprising a primary active ingredient and a dispersing agent and optionally other components wherein at least one component of the composition is liquid and extruding the mix to form an extrudate and drying the extrudate to for granules.

27. A process according to claim 26 which comprises preparing a pre-mix comprising a secondary active ingredient and combining the pre-mix with the dispersing agent and the primary active ingredient to form the mix for extrusion.

28. A water dispersible agrochemical composition comprising a primary agrochemical active ingredient comprising a sulfonyl urea at a level of less than 10% by weight of the composition and a dispersing agent the composition being obtainable by a process comprising preparing a wetted mix in the form of a free-flowing powder comprising the primary active ingredient and the dispersing agent and water, extruding the mix and drying the extrudate to form granules.

29. A composition according to claim 28 wherein the sulfonyl urea comprises bensulfuron-methyl and/or chlorsulfuron.

30. A composition according to claim 28 which further comprises a secondary active ingredient comprising propanil at a level of at least 50% by weight of the composition.

31. A composition according to claim 28 in which the dispersing agent is selected from alkali metal salts of lignosulphonates, naphthalene sulphonate formaldehyde condensates, tristyrylphenol ethoxylate phosphate esters, aliphatic alcohol ethoxylates, alkylphenol ethoxylates, ethylene oxide/propylene oxide (EO-PO) block copolymers, "comb" graft copolymers and polyvinyl alcohol-vinyl acetate copolymers.

* * * * *